(12) United States Patent
Tokoro et al.

(10) Patent No.: US 8,247,074 B2
(45) Date of Patent: Aug. 21, 2012

(54) COATED, FINE METAL PARTICLES COMPRISING SPECIFIC CONTENT OF CARBON AND NITROGEN, AND THEIR PRODUCTION METHOD

(75) Inventors: Hisato Tokoro, Fukaya (JP); Shigeo Fujii, Kumagaya (JP); Takashi Nakabayashi, Kumagaya (JP)

(73) Assignee: Hitachi Metals, Ltd., Tokyo (JP)

( * ) Notice: Subject to any disclaimer, the term of this patent is extended or adjusted under 35 U.S.C. 154(b) by 609 days.

(21) Appl. No.: 12/442,047

(22) PCT Filed: Sep. 18, 2007

(86) PCT No.: PCT/JP2007/068102
§ 371 (c)(1),
(2), (4) Date: Mar. 19, 2009

(87) PCT Pub. No.: WO2008/035681
PCT Pub. Date: Mar. 27, 2008

(65) Prior Publication Data
US 2010/0047579 A1    Feb. 25, 2010

(30) Foreign Application Priority Data

Sep. 20, 2006   (JP) .................................. 2006-254672
Apr. 20, 2007   (JP) .................................. 2007-111342

(51) Int. Cl.
*B32B 5/16*     (2006.01)
*B05D 7/00*     (2006.01)
(52) U.S. Cl. ........................ 428/403; 428/404; 428/701
(58) Field of Classification Search .......... 428/403–407, 428/701
See application file for complete search history.

(56) References Cited

U.S. PATENT DOCUMENTS

| | | | |
|---|---|---|---|
| 4,880,460 A | 11/1989 | Dulis et al. | |
| 4,882,224 A | 11/1989 | Moro et al. | |
| 4,919,734 A | 4/1990 | Ochiai et al. | |
| 6,582,763 B1* | 6/2003 | Nishimura et al. | 427/216 |
| 6,627,313 B2* | 9/2003 | Okinaka et al. | 428/402 |
| 7,285,329 B2* | 10/2007 | Kaneko et al. | 428/403 |
| 7,858,184 B2* | 12/2010 | Tokoro et al. | 428/403 |
| 7,892,316 B2* | 2/2011 | Kaneko et al. | 75/348 |
| 2002/0114800 A1 | 8/2002 | Yamamoto et al. | |
| 2004/0126902 A1 | 7/2004 | Nishiya et al. | |
| 2005/0181202 A1* | 8/2005 | Kaneko et al. | 428/336 |

FOREIGN PATENT DOCUMENTS

| | | |
|---|---|---|
| EP | 0 177 276 A2 | 4/1986 |
| EP | 1 063 639 A1 | 12/2000 |
| FR | 2 817 348 A1 | 5/2002 |
| JP | 2000-030920 A | 1/2000 |
| JP | 2001-078761 A | 3/2001 |
| JP | 2004-135678 A | 5/2004 |
| JP | 2005-120470 A | 5/2005 |
| JP | 2006-097123 A | 4/2006 |

* cited by examiner

*Primary Examiner* — Hoa (Holly) Le
(74) *Attorney, Agent, or Firm* — Sughrue Mion, PLLC (57) ABSTRACT

A method for producing coated, fine metal particles comprising the steps of mixing powder comprising TiC and TiN with powder of an oxide of a metal M meeting the relation of $\Delta G_{M-O} > \Delta G_{TiO_2}$, wherein $\Delta G_{M-O}$ represents the standard free energy of formation of metal M oxide, and heat-treating the resultant mixed powder in a non-oxidizing atmosphere to reduce the oxide of the metal M with the powder comprising TiC and TiN, while coating the resultant metal M particles with Ti oxide, and coated, fine metal particles each comprising a metal core particle and a Ti oxide coating and having a carbon content of 0.2-1.4% by mass and a nitrogen content of 0.01-0.2% by mass.

15 Claims, 5 Drawing Sheets

COATED, FINE METAL PARTICLES COMPRISING SPECIFIC CONTENT OF CARBON AND NITROGEN, AND THEIR PRODUCTION METHOD

CROSS REFERENCE TO RELATED APPLICATIONS

This application is a National Stage of International Application No. PCT/JP2007/068102 filed Sep. 18, 2007, claiming priority based on Japanese Patent Application Nos. 2006-254672 filed Sep. 20, 2006 and 2007-111342 filed Apr. 20, 2007, the contents of all of which are incorporated herein by reference in their entirety.

FIELD OF THE INVENTION

The present invention relates to coated, fine metal particles used for magnetic recording media such as magnetic tapes and magnetic recording discs, electromagnetic wave absorbers, electronic devices (soft magnetic bodies such as yokes) for inductors and printed circuit boards, photocatalysts, nucleic-acid-extracting magnetic beads, medical microspheres, etc., and their production method.

BACKGROUND OF THE INVENTION

As electronic apparatuses and devices have higher performance and smaller size and weight, their materials are required to have higher performance and smaller particle size. For instance, magnetic particles for magnetic tapes are required to have smaller size and improved magnetization to enhance the magnetic recording density.

Also, to separate and collect proteins such as antigens, etc. for the diagnosis of sickness such as allergy, etc., magnetic separation methods have become widely used. As a result, increasingly higher demand is mounting to provide fine magnetic beads having high magnetization and excellent corrosion resistance.

Fine magnetic particles are mainly produced by liquid-phase synthesis methods such as a coprecipitation method, a hydrothermal synthesis method, etc. Fine magnetic particles obtained by the liquid-phase synthesis methods are oxide particles such as ferrite, magnetite, etc. A method of utilizing the thermal decomposition of an organometallic compound has recently become used; and fine magnetic Fe particles are formed, for instance, from $Fe(CO)_6$.

Because magnetic metal particles have larger magnetization than that of oxide particles such as ferrite, their use for industrial applications is greatly expected. For instance, because the metal Fe has saturation magnetization of 218 $Am^2/kg$, much larger than that of iron oxide, it is advantageous in providing excellent magnetic field response and large signal intensity. However, fine metal Fe particles are easily oxidized. When the fine metal Fe particles have a particle size of 100 μm or less, particularly 1 μm or less, they are vigorously burned in the air because of the increased specific surface area, resulting in difficulty in handling in a dry state. Accordingly, oxide particles such as ferrite, magnetite, etc. are widely used.

When the dried fine metal particles are handled, it is necessary to coat the particles lest that the metal is exposed to the air (oxygen). However, the metal would be oxidized considerably even by the method of JP 2000-30920 A, by which the particles are coated with an oxide of the particle-forming metal.

JP 9-143502 A proposes a method for producing graphite-coated, fine metal particles by mixing carbonaceous particles such as carbon black, natural graphite, etc. with particles of a metal or its compound (selected from metal oxides, metal carbides and metal salts), heat-treating the resultant mixture at 1600-2800° C. in an inert gas atmosphere, and cooling it at a speed of 45° C./minute or less. However, because metal-containing particles are heat-treated at an extremely high temperature of 1600-2800° C., this method may suffer the sintering of fine metal particles, and the production efficiency is low. Also, because graphite has a structure in which graphene sheets are laminated, its coating on spherical, fine metal particles inevitably has lattice defects. Accordingly, it is unsatisfactory for applications needing high corrosion resistance, such as magnetic beads, etc. Thus desired are fine metal particles having high corrosion resistance, and a low-cost method for producing such fine metal particles with excellent industrial productivity.

OBJECT OF THE INVENTION

Accordingly, an object of the present invention is to provide coated, fine metal particles having excellent corrosion resistance and high magnetization, and their production method.

DISCLOSURE OF THE INVENTION

As a result of intensive research in view of the above object, the inventors have found that when powder comprising TiC and TiN and powder of metal oxide having higher standard free energy of formation than that of $TiO_2$ are mixed and heat-treated, metal particles coated with Ti oxide are obtained. The present invention has been completed based on such finding.

Thus, the method of the present invention for producing coated, fine metal particles comprises the steps of mixing powder comprising TiC and TiN with powder of an oxide of a metal M meeting the relation of $\Delta G_{M-O} > \Delta G_{TiO2}$, wherein $\Delta G_{M-O}$ represents the standard free energy of formation of metal M oxide, and heat-treating the resultant mixed powder in a non-oxidizing atmosphere to reduce the oxide of the metal M with the powder comprising TiC and TiN, while coating the resultant metal M particles with Ti oxide.

The powder comprising TiC and TiN preferably contains 10-50% by mass of TiN. The TiN content is expressed by the following formula (1):

TiN content (% by mass)=[TiN(% by mass)]/[TiC(% by mass)+TiN(% by mass)]　　(1).

The Ti oxide is preferably based on $TiO_2$.

The heat treatment is preferably conducted at 650-900° C.

In the X-ray diffraction pattern of the coated, fine metal particles, the maximum peak of $TiO_2$ preferably has a half width of 0.3° or less, an intensity ratio of the maximum peak of the metal M to the maximum peak of $TiO_2$ being 0.03 or more. The maximum peak intensity ratio is more preferably 0.05 or more.

The Ti oxide coating based on $TiO_2$ has high crystallinity, sufficiently protecting fine metal core particles. The term "based on $TiO_2$" means that among the measured X-ray diffraction peaks of Ti oxide including other titanium oxides than $TiO_2$ (for instance, $Ti_nO_{2-1}$ having a nonstoichiometric composition), the peak of $TiO_2$ has the maximum intensity. From the aspect of uniformity, it is preferable that the Ti oxide is substantially $TiO_2$. The term "substantially $TiO_2$" means that the percentage of $TiO_2$ is so high that the peaks of other Ti oxides than $TiO_2$ are not clearly discernible in the X-ray diffraction pattern. Accordingly, even if the X-ray diffraction pattern contains peaks of other Ti oxides than $TiO_2$ to such an extent as noise, the condition of "substantially $TiO_2$" is met.

The metal M is preferably a magnetic metal comprising at least one element selected from the group consisting of Fe, Co and Ni, particularly Fe. Because Ti is smaller than Fe in the standard energy of oxide formation, Ti can efficiently and surely reduce Fe oxide. Accordingly, fine, magnetic metal particles having high saturation magnetization and excellent corrosion resistance are obtained. Magnetic beads with magnetic metal cores can be used for magnetic separation.

The oxide of a metal M is preferably $Fe_2O_3$. To obtain coated, fine metal particles having reduced coercivity and increased dispersibility, the ratio of the powder comprising TiC and TiN to the sum of the oxide powder of the metal M and the powder comprising TiC and TiN is preferably 30-50% by mass.

The coated, fine metal particles preferably have saturation magnetization of 50-180 $Am^2/kg$, such that the coating and the magnetic body (magnetic core) have a good quantity balance to provide the coated, fine metal particles with excellent corrosion resistance and magnetic properties. The coated, fine metal particles more preferably has saturation magnetization of 95-180 $Am^2/kg$, which is a range that cannot be obtained by magnetic oxides such as magnetite. The coated, fine metal particles having such magnetic properties exhibit excellent magnetic separation performance.

The coated, fine metal particles preferably has coercivity of 8 kA/m or less, such that they have extremely small residual magnetization, resulting in extremely little magnetic aggregation and excellent dispersibility. The more preferred coercivity is 4 kA/m or less.

Each of the coated, fine metal particles of the present invention comprises a metal core particle and a Ti oxide coating, and has a carbon content of 0.2-1.4% by mass and a nitrogen content of 0.01-0.2% by mass.

The coated, fine metal particles of the present invention preferably have a carbon content of 0.2-1.1% by mass and a nitrogen content of 0.04-0.12% by mass, the total content of carbon and nitrogen being 0.24-0.60% by mass. To obtain particularly high magnetization, the total content of carbon and nitrogen is more preferably 0.25-0.55% by mass.

Each of the coated, fine metal particles of the present invention preferably comprises a metal core particle and a Ti oxide coating, obtained by mixing powder comprising TiC and TiN with powder of an oxide of a metal M meeting the relation of $\Delta G_{M-O} > \Delta G_{TiO2}$, wherein $\Delta G_{M-O}$ represents the standard free energy of formation of metal M oxide, and heat-treating the resultant mixed powder in a non-oxidizing atmosphere to reduce the oxide of the metal M with the powder comprising TiC and TiN, while coating the resultant metal M particles with Ti oxide.

In the coated, fine metal particles of the present invention, the Ti oxide is preferably based on $TiO_2$.

In the coated, fine metal particles of the present invention, the heat treatment is preferably conducted at 650-900° C.

The metal preferably comprises at least one element selected from the group consisting of Fe, Co and Ni. The metal more preferably contains Fe element.

In the quantitative analysis of O, Ti and Fe by X-ray photoelectron spectroscopy of the coated, fine metal particles of the present invention, it is preferable that the Fe content is 14-20 atomic %, and that the ratio of metal Fe is 7-11% of the entire Fe. The inclusion of Fe provides high saturation magnetization.

When 25 mg of the coated, fine metal particles of the present invention are immersed in 1 mL of an aqueous solution of guanidine hydrochloride having a concentration of 6 M at 25° C. for 24 hours, the amount of Fe ions eluted is preferably 50 mg/L or less. The coated, fine metal particles having high corrosion resistance even at a high chaotropic salt concentration are suitable for DNA extraction, etc.

The coated, fine metal particles of the present invention are preferably treated with an alkali.

The coated, fine metal particles of the present invention are preferably further coated with silicon oxide. The coating of silicon oxide provides the coated, fine metal particles with a property as a nucleic-acid-extracting carrier. They also have high corrosion resistance in the fixing treatment with an acid or a base, suitable for the fixing of antibody, etc.

At least one selected from the group consisting of an amino group, a carboxyl group, an aldehyde group, a thiol group, a tosic group and a hydroxyl group is preferably fixed onto the coated, fine metal particles of the present invention. This facilitates the fixing of various materials.

A ligand is preferably fixed onto the coated, fine metal particles of the present invention. Using the specific reaction of a ligand, an objective material can be captured.

The coated, fine metal particles of the present invention are preferably further coated with a blocking agent. The blocking agent suppresses nonspecific adsorption. Surface portions of the coated, fine metal particles, onto which an amino group, a ligand, etc. are not fixed, are preferably coated with the blocking agent.

DESCRIPTION OF THE PREFERRED EMBODIMENTS

[1] Production Method of Coated, Fine Metal Particles

The coated, fine metal particles of the present invention are produced by mixing powder of an oxide of a metal M meeting the relation of $\Delta G_{M-O} > \Delta G_{TiO2}$, wherein $\Delta G_{M-O}$ represents the standard free energy of formation of metal M oxide, with powder comprising TiC and TiN, and heat-treating the resultant mixed powder in a non-oxidizing atmosphere to reduce the oxide of the metal M with the TiC powder and TiN powder, while coating the resultant metal M particles with Ti oxide based on $TiO_2$.

(1) Powder of Oxide of Metal M

The particle size of the powder of an oxide of a metal M may be properly selected depending on the target particle size of the coated, fine metal particles, but it is preferably in a range of 0.001 μm to 5 μm. When the particle size is less than 0.001 μm, secondary aggregation occurs extremely, making it difficult to handle them in the subsequent production steps. When the particle size is more than 5 μm, the metal oxide powder has too small specific surface area, resulting in a slow reduction reaction. The practical particle size of the metal oxide powder is 0.005-1 μm. The metal M is selected from transition metals, precious metals and rare earth metals. As magnetic materials, Fe, Co, Ni and alloys thereof are preferable, and their oxides include $Fe_2O_3$, $Fe_3O_4$, CoO, $Co_3O_4$, NiO, etc. Fe is particularly preferable because of high saturation magnetization, and its oxide is preferably $Fe_2O_3$ because of low cost. Because Ti is lower than Fe in the standard energy of oxide formation, Ti can efficiently and surely reduce Fe oxide.

When the standard free energy of formation ($\Delta G_{M-O}$) of an oxide of a metal M meets the relation of $\Delta G_{M-O} > \Delta G_{TiO2}$, the oxide of a metal M can be reduced by powder comprising TiC and TiN. $\Delta G_{M-O}$ is the standard energy of formation of an oxide of the metal M, and $\Delta G_{TiO2}$ (=−889 kJ/mol) is the standard energy of formation of Ti oxide. For instance, because $Fe_2O_3$ ($\Delta G_{Fe2O3}$=−740 kJ/mol) meets the relation of $\Delta G_{Fe2O3} > \Delta G_{TiO2}$, it is reduced by powder comprising TiC and TiN. When a $TiO_2$ coating is formed by reduction, the specific gravity of the coated, fine metal particles is reduced. Because $TiO_2$ has high hydrophilicity, the $TiO_2$-coated, fine metal particles are suitably dispersed in a solution (water, etc.), for instance, as magnetic beads.

(2) Powder Comprising TiC and TiN

The powder comprising TiC and TiN is used for reducing metal M oxide to form Ti-oxide-coated, fine particles of metal M, in which the amounts of other phases than M and $TiO_2$ are reduced. The use of TiN and TiC reduces the amount of C remaining in the particles.

To conduct a reduction reaction efficiently, the powder comprising TiC and TiN preferably has a particle size of 0.01-20 μm. With the particle size of less than 0.01 μm, it is difficult to handle the powder because it is easily oxidized in the air. When the particle size is more than 20 μm, the reduction reaction does not proceed easily because of a small specific surface area. To conduct the reduction reaction sufficiently while suppressing oxidation in the air, the particle size is particularly 0.1-5 μm.

(3) Reduction Reaction

The ratio of the powder comprising TiC and TiN to the M oxide powder is preferably at least a stoichiometric ratio of the reduction reaction. If Ti lacks, the M oxide powder would be sintered to a bulk during heat treatment.

When both TiC and TiN are used, the TiN content is preferably 10-50% by mass. The TiN content is expressed by the formula (1): TiN content (% by mass)=[TiN(% by mass)]/[TiC(% by mass)+TiN(% by mass)]. When the TiN content is less than 10% by mass, the element C is not fully reduced. The TiN content exceeding 50% by mass provides the lack of C, resulting in insufficient reduction of the oxide to the metal M, thus failing to obtain completely coated, fine metal particles. The mixing of the M oxide powder and the powder comprising TiC and TiN is conducted by a stirring machine such as a mortar, a stirrer, a V mixer, a ball mill, a vibration mill, etc.

When the mixed powder of the M oxide powder and the powder comprising TiC and TiN is heat-treated in a non-oxidizing atmosphere, an oxidation reduction reaction occurs between the M oxide powder and the powder comprising TiC and TiN, forming metal M particles coated with Ti oxide based on $TiO_2$. The heat treatment atmosphere is preferably a non-oxidizing atmosphere, which may be an inert gas such as Ar and He, a gas such as $N_2$, $CO_2$, $NH_3$, etc., though not restrictive. The heat treatment temperature is preferably 650-900° C. When it is lower than 650° C., the reduction reaction does not sufficiently proceed. When it is higher than 900° C., $Ti_nO_{2n-1}$ having a nonstoichiometric composition is formed. $Ti_nO_{2n-1}$ is formed by the removal of oxygen by the metal M from $TiO_2$ at higher than 900° C., or by the release of oxygen by $TiO_2$ into the non-oxidizing atmosphere. As a result, the oxide of the metal M is insufficiently reduced, or an insufficient coating is formed. When the heat treatment temperature is 650-900° C., a highly uniform coating substantially based on $TiO_2$ and having less defects is formed. The $TiO_2$ coating is suitable for coated, fine metal particles as a photocatalyst.

(4) Magnetic Separation

Because the coated, fine, magnetic metal particles may contain non-magnetic components (particles made only of $TiO_2$-based Ti oxide), a magnetic separation operation is preferably conducted plural times with a permanent magnet, if necessary, to collect only magnetic particles.

[2] Structure and Properties of Coated, Fine Metal Particles (1) Particle Size of Coated, Fine Metal Particles The coated, fine metal particles obtained by the above method have particle size variable depending on the particle size of the M oxide powder. To obtain high corrosion resistance and dispersibility, the median diameter d50 of the coated, fine metal particles is preferably 0.1-10 μm, more preferably 0.1-6 μm. When the median diameter is less than 0.1 μm, the coated, fine metal particles do not have sufficiently thick coatings, resulting in low corrosion resistance, and extremely small magnetization per one particle, which leads to slow magnetic response. When the median diameter d50 is more than 10 μm, the coated, fine metal particles have low dispersibility in a liquid. The median diameter d50 is a 50-%-cumulative particle size in a cumulative distribution curve obtained from the particle size distribution (on a volume basis) measured by a wet-type laser diffraction particle size analyzer.

(2) Coating Structure

The M metal particles and the Ti oxide coating need not have a 1:1 core-shell structure, but may have a structure in which 2 or more M metal particles are dispersed in the Ti oxide based on $TiO_2$. The inclusion of 2 or more M metal particles in the Ti oxide is preferable because a high-content metal M is surely coated. In the method of the present invention, the reduction of the M oxide forms fine M metal particles and Ti oxide coatings simultaneously, there is no M metal oxide layer between the fine M metal particle and the Ti oxide coating. The Ti oxide coating obtained by a heat treatment at 650° C. or higher has high crystallinity, and higher corrosion resistance than that of amorphous or low-crystallinity Ti oxide coatings formed by a sol-gel method, etc. Because the coated, fine metal particles of the present invention each having a $TiO_2$-based coating have less coating defects, thus higher in corrosion resistance than those having a $Ti_nO_{2n-1}$ coating having a nonstoichiometric composition.

(3) Coating Thickness

The Ti oxide coating based on $TiO_2$ preferably has a thickness of 1-10000 nm. When the thickness is less than 1 nm, the coated, fine metal particles do not have sufficient corrosion resistance. When the thickness is more than 10000 nm, the coated, fine metal particles are too large, having low dispersibility in a liquid, and having low saturation magnetization for fine, magnetic metal particles. The Ti oxide coating is more preferably as thick as 5-5000 nm. The coating thickness is determined from the transmission electron photomicrograph of the coated, fine metal particles. When the Ti oxide coating has uneven thickness, an average of the maximum thickness and the minimum thickness is regarded as the thickness of the Ti oxide coating. The fine metal particles need not be coated with $TiO_2$-based Ti oxide completely, but may be exposed to the surface partially, though complete coating is preferable.

(4) Crystallinity of Ti Oxide

In the X-ray diffraction pattern of the coated, fine metal particles, when the half width of the maximum peak of $TiO_2$ is 0.3° or less, and when the intensity ratio of the maximum peak of $TiO_2$ to the maximum peak of the metal M is 0.03 or more, the Ti oxide has such high crystallinity that the coated, fine metal particles are corrosion-resistive. When $TiO_2$ is amorphous or low-crystallinity, diffraction peaks are not observed or broad. Accordingly, the maximum peak intensity ratio is small with a large half width. The maximum peak intensity ratio is more preferably 0.05 or more. A higher maximum peak intensity ratio (higher coating ratio) provides lower saturation magnetization. Thus, the maximum peak intensity ratio is preferably 3 or less.

(5) Function as Magnetic Particles

When the metal M is magnetic Fe, the coated, fine metal particles obtained by the above method have saturation magnetization in a range of 50-180 $Am^2/kg$, functioning as magnetic particles. This corresponds to a case where a ratio of Ti to (Fe+Ti) is 11-67% by mass when the coated, fine metal particles are composed of magnetic metal Fe and $TiO_2$. When the X-ray diffraction pattern confirms that the coated, fine metal particles are constituted by Fe and $TiO_2$, the ratio of Ti can be calculated from the measured saturation magnetization of the coated, fine metal particles. When the saturation magnetization of the magnetic particles is as small as less than 50 $Am^2/kg$, they have slow response to a magnetic field. When the saturation magnetization is more than 180 $Am^2/kg$, the ratio of $TiO_2$-based Ti oxide is small [a mass ratio of Ti to (Fe+Ti) is less than 11%], meaning that the metal Fe particles are not fully coated with Ti oxide. Accordingly, the coated, fine metal particles have low corrosion resistance, and their magnetic properties are easily deteriorated. To obtain high saturation magnetization and sufficient corrosion resistance simultaneously, the coated, fine metal particles preferably have saturation magnetization of 180 $Am^2/kg$ or less. To have excellent recovery efficiency and magnetic separation performance when used for magnetic beads, etc., the coated, fine metal particles more preferably have saturation magnetization of 95-180 $Am^2/kg$. Saturation magnetization in this range cannot be achieved by magnetite ($Fe_3O_4$) having as small saturation magnetization as about 92 $Am^2/kg$. For dispersibility, the coercivity of the coated, fine metal particles is preferably 15 kA/m or less, more preferably 8 kA/m (100 Oe) or less, most preferably 4 kA/m or less. Although thick $TiO_2$ coatings would provide high dispersibility even with large coercivity, they would reduce the saturation magnetization of the coated, fine metal particles. When the coercivity is more than 8 kA/m, magnetic particles are magnetically aggregated without a magnetic field, resulting in low dispersibility in a liquid.

(6) Concentrations of Elements Contained

The coated, fine metal particles preferably contain 0.2-1.4% by mass of C. C is a residue of the TiC powder used as a starting material. In the method of the present invention for reducing the metal M oxide with Ti as a reducing agent to a metal M, C in TiC also functions as a reducing agent, auxiliarily reducing the metal M oxide. Less than 0.2% by mass of C is not preferable because the M oxide is not fully reduced. More than 1.4% by mass of C leads to the reduced metal content, and low saturation magnetization when the metal is based on at least one element selected from the group consisting of Fe, Co and Ni. The remaining C makes the coated, fine metal particles hydrophobic, resulting in low dispersibility in an aqueous solution, which is particularly unpreferable as magnetic beads, etc. The C content is more preferably 0.2-1.1% by mass.

The coated, fine metal particles preferably contain 0.01-0.2% by mass of N. N is derived from the nitriding of excess Ti during a heat treatment, and the residue of the TiN powder after the heat treatment. Less than 0.01% by mass of N is not preferable because the reducing effect of TiN is not obtained. More than 0.2% by mass of N undesirably leads to increase in non-magnetic titanium nitride and low saturation magnetization. To sufficiently coat fine metal M core particles, it is preferable that Ti exists excessively to some extent, such that part of Ti is nitrided during the heat treatment. The N content is more preferably 0.04-0.2% by mass.

To keep higher saturation magnetization, it is important to control the total amount of C and N contained in the coated, fine metal particles in a predetermined range; the total amount (C+N) of C and N contained is preferably 0.24-1.6% by mass, more preferably 0.24-0.60% by mass. When (C+N) is less than 0.24% by mass, C and N are outside above preferred ranges. (C+N) exceeding 1.6% by mass invites the reduction of saturation magnetization. To provide sufficient coating to fine metal M particles while achieving high saturation magnetization, (C+N) is particularly 0.60% or less by mass.

The C content in the above coated, fine metal particles is measured by high-frequency-heated infrared absorption, and the N content is measured by a thermal conduction method with heating in an inert gas or a Kjeldahl method.

(7) Corrosion Resistance

When 25 mg of coated, fine Fe particles are immersed in 1 mL of an aqueous solution of guanidine hydrochloride having a molar concentration of 6 M at 25° C. for 24 hours, the amount of Fe ions eluted is preferably 50 mg/L or less. Because coated, fine metal particles with such amount of Fe ions eluted have high corrosion resistance even at a high concentration of a chaotropic salt, they are suitable for DNA extraction, etc. needing a treatment in an aqueous chaotropic salt solution. Although such corrosion resistance that the amount of Fe ions eluted is 50 mg/L or less can be obtained without an alkali treatment, the alkali treatment is preferable to surely obtain the above corrosion resistance level. As is clear from the descriptions concerning "corrosion resistance" and "X-ray diffraction" in the specification, the coated, fine metal particles of the present invention include assembly (powder) of coated, fine metal particles.

(8) Surfaces of Coated, Fine Metal Particles

To provide properties as a nucleic-acid-extracting carrier, each coated, fine metal particle is preferably a silicon-oxide-based coating. The outermost coating can be formed by the hydrolysis of metal alkoxide. It is obtained by, for instance, the hydrolysis reaction of silicon alkoxide. Specific examples of silicon alkoxides include tetramethoxysilane, tetraethoxysilane, aminopropyltrimethoxysilane, etc. Silicon oxide is obtained, for instance, by the hydrolysis reaction of tetraethoxysilane with good reproducibility.

At least one of an amino group, a carboxyl group, an aldehyde group, a thiol group, a tosic group, and a hydroxyl group is preferably fixed to the surfaces of the coated, fine metal particles. With such functional group fixed, various ligands can be easily attached. Also, the fixing of the functional group can adjust dispersibility in a solution.

A ligand is preferably fixed to the surfaces of the coated, fine metal particles. The ligand is a substance specifically bonding to a particular substance. The ligand may be avidin, biotin, streptavidin, secondary antibodies, protein Q protein A, protein A/I, protein L, antibodies, antigens, lectins, sugar chains, hormones, nucleic acids, etc. These materials may be fixed alone or in combination. With avidin or streptavidin fixed to the surfaces of the coated, fine metal particles, the coated, fine metal particles can specifically bond to biotin-labeled materials, such as biotin-labeled antibodies, biotin-labeled DNAs and biotin-labeled fluorescent materials. Because avidin and streptavidin have four bonding sites to biotin, avidin or streptavidin can bond to the biotin-fixed, coated, fine metal particles, and further to a biotin-labeled material. Because the secondary antibody selectively bonds to a particular antibody, it can fix a primary antibody. Because the protein G strongly bonds to Fc of immunoglobulin G (IgG), it can selectively bond to IgG. The protein A exhibits largely different bonding to various types of IgG, selectively bonding to particular IgG Because the bonding of the protein A to IgG depends on pH, the once-captured IgG can be dissociated by changing pH. Accordingly, the protein-A-fixed, coated, fine metal particles are suitable for the purification of IgG, etc. The protein A/G is a fusion protein of the protein A and the protein G, suitable as a ligand. Because the protein L bonds to other Ig than those of cow, goat, sheep and hen, it can selectively capture other Ig than those of cow, goat, sheep and hen in serum containing Ig of cow, goat, sheep or hen. The antibody and the antigen selectively bond to each other by an antigen-antibody reaction. The coated, fine metal particles, to which antibody or antigen is fixed, are suitable for an immunological measurement method (immunoassay). Because the antibodies, antigens, lectins, sugar chains and hormones can specifically capture particular materials, they are suitable for the collection of proteins, cells, etc. For instance, with a desired nucleic acid or a nucleic acid complimentary to part of the desired nucleic acid fixed to the coated, fine metal particles, the desired nucleic acid can be selectively collected.

The coated, fine metal particles are preferably coated with a blocking agent to suppress nonspecific adsorption. The nonspecific adsorption (nonspecificity) is the adsorption of other materials than those desired. The blocking agents include bovine serum albumin (BSA), skim milk, etc. Commercially available blocking agents can be used, for instance, Block Ace (Snow Brand Milk Products Co., Ltd.), etc. for suppressing nonspecific adsorption.

The present invention will be explained in further detail by Examples below without intention of restricting the present invention thereto.

REFERENCE EXAMPLE 1

Figure 1:
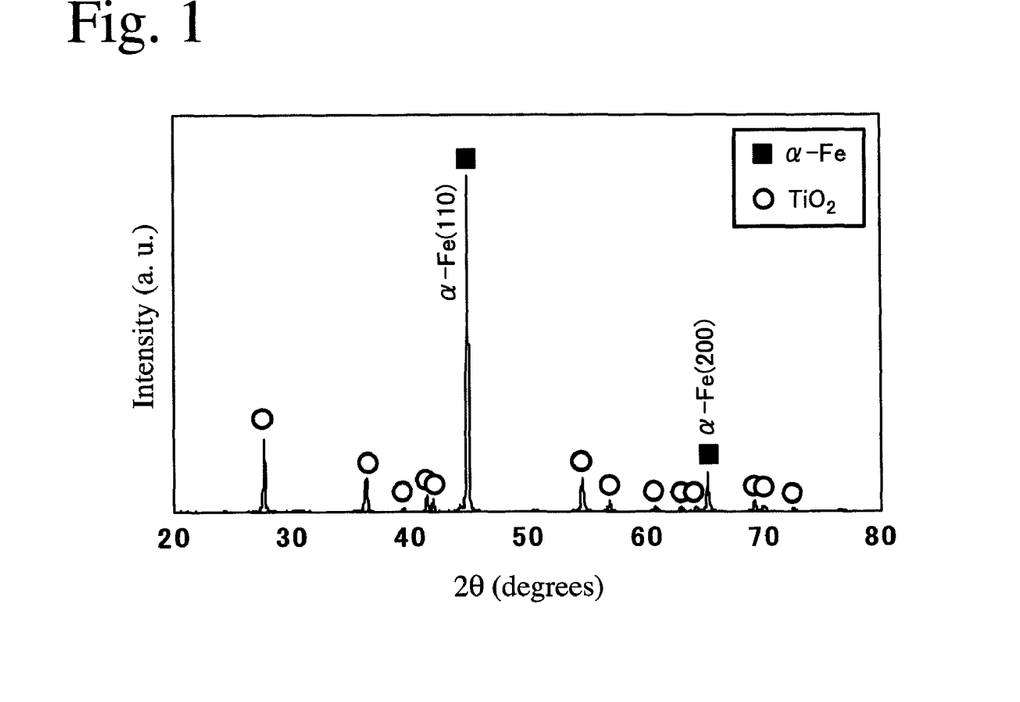
FIG. 1 is a graph showing the X-ray diffraction pattern of the powder sample of Reference Example 1.

$\alpha$-$Fe_2O_3$ powder having a median diameter of 0.03 μm and TiC powder having a median diameter of 1 μm were mixed at a mass ratio of 7:3 for 10 hours by a ball mill, and the mixed powder was heat-treated at 700° C. for 2 hours in a nitrogen gas in an alumina boat. The X-ray diffraction pattern of the resultant powder sample is shown in FIG. 1. In FIG. 1, the axis of abscissas represents a diffraction angle 2θ (°), and the axis of ordinates represents diffraction intensity (relative value). Analysis using analysis software "Jade, Ver.5" available from MDI revealed that it had diffraction peaks assigned to α-Fe and rutile $TiO_2$.

Calculation from the half width of a (200) peak of α-Fe using a Scherrer's equation revealed that Fe had an average crystallite size of 90 nm. The maximum diffraction peak of $TiO_2$ obtained at 2θ=27.5° had a half width of 0.14, and an intensity ratio of the maximum diffraction peak of $TiO_2$ to the maximum diffraction peak [(110) peak] of α-Fe was 0.18. This verifies that $TiO_2$ had high crystallinity. Measurement by a laser-diffraction particle size distribution meter ("LA-920" available from HORIBA) revealed that this powder sample had a median diameter d50 of 3.1 μm.

Figure 2:
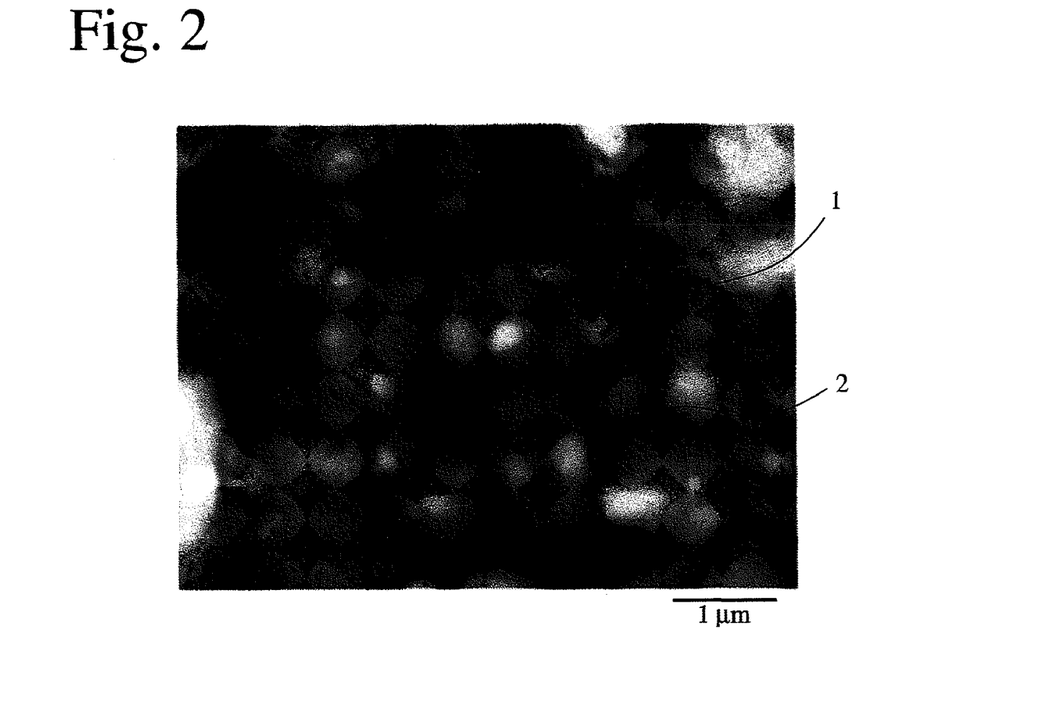
FIG. 2 is a scanning electron photomicrograph of the powder sample of Reference Example 1.

It is clear from the SEM photograph shown in FIG. 2 that the coated, fine metal particles had diameters of several μm. In most coated, fine metal particles, pluralities of Fe particles 2 were coated with a $TiO_2$ layer 1 to form one fine particle. For instance, Fe particles 2 (white portions in FIG. 2) contained in the $TiO_2$ layer shown by an arrow 1 had diameters of about 0.5 μm.

Because Fe oxide has a standard energy of formation $\Delta G_{Fe2O3}$ of −740 kJ/mol, and Ti oxide has $\Delta G_{TiO2}$ of −889 kJ/mol, the latter is smaller than the former. It is thus considered that α-$Fe_2O_3$ was reduced by TiC to form $TiO_2$.

5 g of the resultant powder sample and 50 mL of isopropyl alcohol (IPA) were charged into a 100-mL beaker, and subjected to ultrasonic irradiation for 10 minutes. With a permanent magnet in contact with an outer surface of the beaker for 1 minute, only magnetic particles were adsorbed to an inner surface of the beaker, and dark gray supernatant liquid was removed. This magnetic separation operation was repeated 50 times, and the purified magnetic particles were dried at room temperature. The magnetic properties of the magnetic particles were measured by VSM (vibrating sample magnetometer) in a maximum magnetic field of 1.6 MA/m. After it was confirmed from their X-ray diffraction pattern that the coated, fine metal particles were constituted by Fe and $TiO_2$, an Fe/Ti mass ratio in the purified magnetic particles was calculated from the measured value of saturation magnetization of the coated, fine metal particles. The results are shown in Table 1.

REFERENCE EXAMPLES 2-5

Powder samples were produced and purified to obtain magnetic particles in the same manner as in Reference Example 1, except for changing a mass ratio of α-$Fe_2O_3$ powder to TiC powder as shown in Table 1. The compositions and magnetic properties of these magnetic particles were measured in the same manner as in Reference Example 1. The results are shown in Table 1.

The magnetic particles of Reference Example 5, in which a mass ratio of α-$Fe_2O_3$ powder to TiC powder was 4:6, had high corrosion resistance, saturation magnetization Ms of 48 $Am^2/kg$, lower than 50 $Am^2/kg$, and coercivity iHc of 18 kA/m, more than 15 kA/m. It is thus clear that the TiC content is preferably 30-50% by mass to keep high saturation magnetization without losing the properties of metal Fe particles.

TABLE 1

| No. | Mass Ratio[1] of $Fe_2O_3$:TiC | Mass Ratio[2] of Fe:Ti | Magnetic Properties | |
|---|---|---|---|---|
| | | | Ms ($Am^2/kg$) | iHc (kA/m) |
| Reference Example 1 | 7:3 | 71:29 | 130 | 3.8 |

TABLE 1-continued

| No. | Mass Ratio[1] of $Fe_2O_3$:TiC | Mass Ratio[2] of Fe:Ti | Magnetic Properties | |
|---|---|---|---|---|
| | | | Ms ($Am^2$/kg) | iHc (kA/m) |
| Reference Example 2 | 6.5:3.5 | 66:34 | 116 | 6.2 |
| Reference Example 3 | 6:4 | 60:40 | 103 | 8.5 |
| Reference Example 4 | 5:5 | 47:53 | 75 | 13 |
| Reference Example 5 | 4:6 | 32:68 | 48 | 18 |

Note:
[1] A mass ratio of α-$Fe_2O_3$ to TiC in the starting material (mixed powder).
[2] A mass ratio of Fe to Ti in the purified magnetic particles.

REFERENCE EXAMPLE 6

Coated, fine, magnetic metal particles were obtained in the same manner as in Reference Example 1 except that the heat treatment temperature was 800° C. The magnetic properties of this powder sample were measured in the same manner as in Reference Example 1. The C content in the powder sample was measured by a high-frequency-heated infrared absorption method using "EMIA-520" available from HORIBA, and the N content was measured by a heat conduction method in which heating was conducted in an inert gas, using "EMGA-1300" available from HORIBA. The results are shown in Table 2.

EXAMPLES 1-5

Coated, fine, magnetic metal particles were obtained in the same manner as in Reference Example 6 except for substituting part of the TiC powder with TiN powder having a median diameter of 2.8 μm at the ratio shown in Table 2. The magnetic properties, C content and N content of these powder samples were evaluated in the same manner as in Reference Example 6. The results are shown in Table 2.

TABLE 2

| No. | Formulation of Starting Materials (% by mass) | | | TiN Content (% by mass) | Magnetic Properties | | Content (% by mass) | |
|---|---|---|---|---|---|---|---|---|
| | $Fe_2O_3$ | TiC | TiN | | Ms ($Am^2$/kg) | iHc (kA/m) | C | N |
| Reference Example 6 | 70 | 30 | 0 | 0 | 136 | 5.3 | 1.7 | 0.23 |
| Example 1 | 70 | 27 | 3 | 10 | 140 | 5.2 | 1.4 | 0.17 |
| Example 2 | 70 | 24 | 6 | 20 | 143 | 5.2 | 1.1 | 0.12 |
| Example 3 | 70 | 21 | 9 | 30 | 151 | 4.7 | 0.9 | 0.09 |
| Example 4 | 70 | 18 | 12 | 40 | 158 | 4.5 | 0.5 | 0.04 |
| Example 5 | 70 | 15 | 15 | 50 | 106 | 1.6 | 0.2 | 0.04 |

As the amount of TiN increased, the contents of C and N decreased, and the saturation magnetization Ms was improved. Particularly when the TiN content was 20-40% by mass (Examples 2-4), the C content was 1.3% by mass or less, and the N content was 0.2% by mass or less, their contents being extremely small. Example 4 having a TiN content of 40% by mass exhibited Ms improved to 158 $Am^2$/kg. However, Example 5 having a TiN content of 50% by mass had rather smaller Ms than that of Reference Example 6 containing no TiN, despite small contents of C and N. This appears to be due to the fact that a too small amount of C made a reduction reaction insufficient. However, the coated, fine, magnetic metal particles of Example 5 had extremely small coercivity iHc, resulting in smaller residual magnetization and suppressed magnetic aggregation. Thus, it is suitable for applications needing redispersibility, such as magnetic beads, etc.

EXAMPLES 6-11

Coated, magnetic metal particles were obtained in the same manner as in Example 4 except for mixing starting materials for the period of time shown in Table 3 using a bead mill. The median diameter d50 of this magnetic powder was measured by a laser-diffraction particle size distribution meter ("LA-920" available from HOLIBA). The results are shown in Table 3. Table 3 also shows their magnetic properties and their C and N contents. The C content was measured in the same manner as in Reference Example 6, using "HFT-9" available from Kokusai Denshi Kogyo KK. The N content was measured by a Kjeldahl method comprising converting N contained in the sample to ammonia, and measuring ammonia by indophenol blue absorptiometry using a spectrophotometer ("UV-1600" available from Shimadzu Corporation). The contents of C and N in these Examples were lower than those shown in Table 2 as a whole; C being 0.24-0.54% by mass, and N being 0.01-0.02% by mass. The total content of C and N was 0.26% by mass at minimum in Example 9, and 0.55% by mass at maximum in Example 11.

TABLE 3

| No. | Mixing Time (min) | Median Diameter (μm) | Magnetic Properties | | Content (% by mass) | |
|---|---|---|---|---|---|---|
| | | | Ms ($Am^2$/kg) | iHc (kA/m) | C | N |
| Example 6 | 90 | 2.0 | 130 | 1.7 | 0.29 | 0.01 |
| Example 7 | 120 | 1.6 | 129 | 1.8 | 0.28 | 0.02 |
| Example 8 | 150 | 1.1 | 128 | 1.9 | 0.27 | 0.02 |
| Example 9 | 180 | 1.0 | 127 | 2.0 | 0.24 | 0.02 |
| Example 10 | 210 | 0.86 | 125 | 2.2 | 0.33 | 0.02 |
| Example 11 | 240 | 0.92 | 133 | 2.0 | 0.54 | 0.01 |

The powder samples of Reference Example 6 and Examples 2-4 were analyzed by X-ray photoelectron spectroscopy (XPS) using PHI-Quantera SXM available from ULVAC-PHI, Inc. Narrow spectra were measured with respect to 1s-orbital electrons of O, 2p3-orbital electrons of Fe, and 2p-orbital electrons of Ti, to carry out quantitative analysis. The results are shown in Table 4.

TABLE 4

| No. | TiN Content (% by mass) | Elements (atomic %) | | | Metal Fe/Total Fe (%) |
|---|---|---|---|---|---|
| | | O | Fe | Ti | |
| Reference Example 6 | 0 | 72.4 | 13.1 | 14.5 | 4.3 |
| Example 2 | 20 | 72.6 | 14.0 | 13.4 | 6.6 |
| Example 3 | 30 | 73.1 | 13.3 | 13.6 | 6.5 |
| Example 4 | 40 | 72.9 | 19.6 | 7.6 | 11.3 |

Increase in the TiN content resulted in the increase of the Fe content and the decrease of the Ti content. Namely, the addition of TiN increased the Fe content. This means that a Ti oxide layer became thinner. However, coating layers on the Fe cores were not insufficient, because the percentage of Fe oxide did not increase as described later. It is considered that the magnetic properties were improved because the volume of a non-magnetic coating was kept minimum while fully coating Fe particles. Increase in the TiN content resulted in the decrease of the Fe oxide and the increase of the metal Fe. Particularly when the TiN content was 20-40% by mass, the ratio of metal Fe (metal Fe/total Fe) was 6% or more. This is due to the fact that the addition of TiN provided such a complete Ti oxide coating that metal Fe was not oxidized though it was thin.

REFERENCE EXAMPLE 7, AND EXAMPLES 12-14

1 g of each powder sample obtained in Reference Example 6 and Examples 2-4 was added to 50 mL of an aqueous solution of NaOH (concentration 1 M), to conduct an immersion treatment (alkali treatment) at 60° C. for 24 hours. After this alkali treatment, each powder sample was washed with water and dried. 25 mg of each powder sample was immersed in 1 mL of an aqueous solution of guanidine hydrochloride (concentration 6 M) at 25° C. for 24 hours (immersion test), and then the amount of Fe ions eluted was measured by an ICP analyzer ("SPS3100H" available from SII NanoTechnology Inc.). The results are shown in Table 5.

TABLE 5

| No. | Powder Sample Used | TiN Content (% by mass) | Amount of Fe Ions Eluted (mg/L) | |
|---|---|---|---|---|
| | | | Before Alkali Treatment | After Alkali Treatment |
| Reference Example 7 | Reference Example 6 | 0 | 200 | 21 |
| Example 12 | Example 2 | 20 | 170 | 16 |
| Example 13 | Example 3 | 30 | 150 | 14 |
| Example 14 | Example 4 | 40 | 7.2 | 6.2 |

The amount of Fe ions eluted was reduced to 50 mg/L or less by the alkali treatment. The larger the TiN content, the smaller the amount of Fe ions eluted. Particularly at the TiN content of 40% by mass, the amount of Fe ions eluted was as extremely small as less than 10 mg/L even before the alkali treatment, indicating excellent corrosion resistance.

With respect to the coated, fine metal particles of Examples 6-11 shown in Table 3, the amount of Fe ions eluted was measured in the same manner as in Reference Example 7 without alkali treatment. The results are shown in Table 6. The amount of Fe ions eluted was 2.1 mg/L or less, indicating excellent corrosion resistance.

TABLE 6

| No. | Amount of Fe Ions Eluted (mg/L) |
|---|---|
| Example 6 | 1.0 or less |
| Example 7 | 1.0 or less |
| Example 8 | 1.3 |
| Example 9 | 1.6 |
| Example 10 | 2.1 |
| Example 11 | 1.1 |

The same X-ray diffraction measurement as in Reference Example 1 revealed that any powder sample obtained in Examples 1-5 and 12-14 and Reference Example 7 had a half width of 0.3° or less in the maximum peak of $TiO_2$, and an intensity ratio (maximum peak of $TiO_2$/maximum peak of metal M) of 0.03 or more.

EXAMPLE 15

The coated, fine metal particles obtained in Example 4 were coated with silica by a method described below, to provide magnetic silica particles. 5 g of the above coated, fine metal particles (powder sample) were dispersed in 100 mL of ethanol, and 1 mL of tetraethoxysilane was added thereto. While stirring, the resultant dispersion was mixed with a mixture solution of 22 g of pure water and 4 g of ammonia water (25%), and stirred for 1 hour. After stirring, a supernatant liquid was removed with the magnetic particles held on an inner surface of the beaker by a magnet. After the magnetic particles thus obtained were subjected to the above silica coating treatment 2 times, the solvent was substituted with isopropyl alcohol, and the magnetic particles were dried to obtain magnetic silica particles.

The performance of the magnetic silica particles as magnetic beads was evaluated by measuring the amount of DNA extracted from 100 µL of horse blood using a DNA extraction kit ("MagNA Pure LC DNA Isolation Kit I" available from Roche). DNA was extracted according to the protocol of the above Kit except for using a solution obtained by dispersing 12 mg of magnetic silica particles in 150 µL of isopropyl alcohol (IPA) as a liquid of magnetic beads. The amount of DNA in the resultant extract was measured by a UV spectrophotometer [photodiode array bio-spectrophotometer ("U-0080D" available from Hitachi High-Technologies Corporation)]. As a result, the amount of DNA extracted from 100 µL of horse blood was 2.7 µg.

COMPARATIVE EXAMPLE 1

Using commercially available magnetic beads attached to MagNAPure LC DNA Isolation Kit I available from Roche, DNA was extracted in the same manner as in Example 15. As a result, the amount of DNA extracted was 2.7 µg.

It is clear from above that the coated, fine metal particles of the present invention are suitable as magnetic beads.

EXAMPLE 16

Coated, fine metal particles were produced in the same manner as in Example 4 except that the mixing time of starting material powder was 100 minutes, and provided with a silica coating in the same manner as in Example 15 to obtain magnetic silica particles. The median diameter d50, specific surface area and magnetic properties of the magnetic silica particles are shown in Table 7. The specific surface area was measured by a BET method with nitrogen adsorption, using "Macsorb-1201" available from Mountech Co., Ltd.

EXAMPLE 17

Coated, fine metal particles were produced in the same manner as in Reference Example 6 except that the mixing time of starting material powders was 100 minutes, and provided with silica coating in the same manner as in Example 15 to obtain magnetic silica particles. The median diameter d50, specific surface area and magnetic properties of the magnetic silica particles were evaluated in the same manner as in Example 16. The results are shown in Table 7.

Commercially available magnetic beads used in Comparative Example 1 were measured with respect to these properties. The results are shown in Table 7. The magnetic beads of Examples 16 and 17 were smaller in particle size, higher (2 times or more) in saturation magnetization, and lower (about 1/10) in coercivity than those of Comparative Example 1.

TABLE 7

| No. | d50 (μm) | Specific Surface Area (m²/g) | Ms (Am²/kg) | iHc (kA/m) |
|---|---|---|---|---|
| Example 16 | 7.6 | 2.3 | 112 | 1.6 |
| Example 17 | 8.3 | 2.8 | 106 | 3.7 |
| Comparative Example 1 | 13 | 8.3 | 43.7 | 12 |

The magnetic beads used in Examples and Comparative Example in Table 7 were evaluated with respect to the performance of extracting DNA from human whole blood. DNA was extracted from whole blood in the same manner as in Example 15, except that 100 μL of human whole blood was tested, and that the amount (mass) of magnetic silica particles used was changed as shown in Table 8. The amount of DNA in the extract was determined by labeling DNA with a fluorescent reagent intercalating into double-stranded DNA, and measuring its fluorescence intensity by the following method. Namely, 2 μL of a DNA extract liquid was mixed with 198 μL of a 200-times-diluted solution of a fluorescent reagent ("PicoGreen" available from Invitrogen Japan K.K.) [diluted with a TE solution (10 mM of Tris-HCl and 1 mM of EDTA)], to react DNA with the fluorescent reagent, and its fluorescence intensity was measured by a fluorescence spectrophotometer ("F-4500" available from Hitachi Ltd.). Excited with light having a wavelength of 480 nm, the fluorescence intensity at a wavelength of 520 nm was measured. The amount of DNA extracted in each magnetic bead sample is shown in Table 8. The amount of DNA extracted per a unit surface area of each magnetic silica particle sample, which was calculated from the specific surface area shown in Table 7, is shown in Table 8.

Comparison on the same mass (12 mg) revealed that Example 16 was as much as about 2.7 times Comparative Example 1 in the amount of DNA extracted per a unit area. Even when the amount of beads used was reduced to 2 mg (the amount of DNA extracted per a unit area was about 6 times when it was 12 mg), the amount of DNA extracted was stable at about 2 μg. Because the magnetic silica particles of Example 16 had a smaller median diameter and a larger surface area effective for DNA extraction than those of Comparative Example 1, the former can extract DNA sufficiently even with a small amount of beads. Also, because of high saturation magnetization (see Table 7), the magnetic beads of Example 16 capturing DNA are magnetically collected with high efficiency, and suffer extremely small loss in a washing step, etc. Accordingly, the magnetic beads of Example 16 are sufficiently higher than those of Comparative Example 1 in the amount of DNA extracted per a unit area. The magnetic silica particles of Example 17 were slightly poorer than those of Example 16, but exhibited higher DNA-extracting performance than those of Comparative Example 1.

TABLE 8

| Sample | Mass of Beads (mg) | Amount of DNA Extracted (μg) | Per Unit Area (μg/m²) |
|---|---|---|---|
| Example 16 | 2 | 2.15 | 0.47 |
| | | 1.90 | 0.41 |
| | 4 | 2.24 | 0.24 |
| | | 2.22 | 0.24 |
| | 6 | 2.58 | 0.19 |
| | | 2.40 | 0.17 |
| | 12 | 2.15 | 0.078 |
| | | 2.38 | 0.086 |
| | 24 | 2.18 | 0.040 |
| | | 2.14 | 0.039 |
| | 48 | 1.80 | 0.016 |
| | | 1.93 | 0.017 |
| Example 17 | 2 | 0.98 | 0.17 |
| | | 1.04 | 0.19 |
| | 4 | 1.86 | 0.17 |
| | | 1.92 | 0.17 |
| | 6 | 2.07 | 0.12 |
| | | 2.67 | 0.16 |
| | 12 | 1.89 | 0.056 |
| | | 2.12 | 0.063 |
| | 24 | 2.35 | 0.035 |
| | | 1.87 | 0.028 |
| | 48 | 2.20 | 0.016 |
| | | 2.27 | 0.017 |
| Comparative Example 1 | 12 | 2.84 | 0.028 |
| | | 3.14 | 0.032 |

EXAMPLE 18

Figure 3:
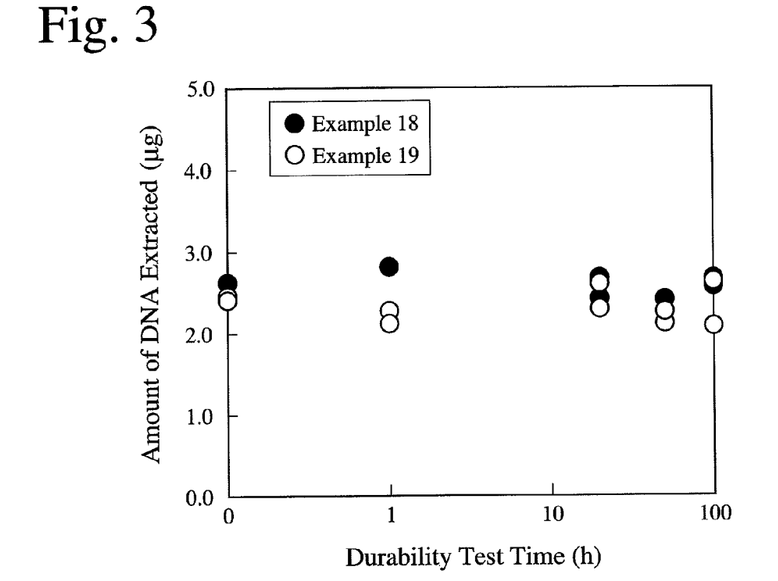
FIG. 3 is a graph showing the relation between the amount of DNA extracted and the durability test time in Examples 18 and 19.

The coated, fine metal particles of Example 11 were coated with silica to obtain magnetic silica particles in the same manner as in Example 15. To evaluate the performance stability of the magnetic silica particles as magnetic beads, a durability test described below was conducted, and the DNA-extracting performance of the magnetic silica particles was evaluated after the test. The durability test was conducted by charging 0.32 g of magnetic silica particles and 4 mL of isopropyl alcohol (IPA) into a screw-cap bottle having a volume of 6 mL, and keeping it at 60° C. for 1 hour, 10 hours, 50 hours and 100 hours, respectively. While magnetic beads are usually stored at room or lowered temperature, keeping the temperature at 60° C. causes forced deterioration for durability evaluation. Using the magnetic beads after the durability test, DNA was extracted from 100 μL of horse blood in the same manner as in Example 10. FIG. 3 shows the relation between the amount of DNA extracted and the durability test time.

EXAMPLE 19

The coated, fine metal particles obtained in Example 11 were coated with silica to obtain magnetic silica particles in the same manner as in Example 15, except for adding 0.05 g of aluminum isopropoxide (corresponding to 5% by mass of tetraethoxysilane) together with 1 mL of tetraethoxysilane. The magnetic silica particles were subjected to the same durability test as in Example 18, and their DNA-extracting performance after the durability test was evaluated to examine the stability of performance as magnetic beads. The results are shown in FIG. 3.

The amount of DNA collected was stable in both Examples 18 and 19, resulting in substantially no change in the amount of DNA collected even after 100 hours of immersion in IPA (24-times-accelerated test relative to storing at room temperature). Namely, the magnetic silica particles of Examples 18 and 19 had excellent durability of DNA-extracting performance. This means that the coated, fine metal particles were neither modified nor deteriorated even by heating at 60° C. in IPA because of excellent corrosion resistance as shown in Table 3. Namely, the magnetic silica particles of the present invention exhibit stable DNA-extracting performance, and excellent long-term stability of performance as magnetic beads.

EXAMPLE 20

Coated, fine, magnetic metal particles were obtained in the same manner as in Example 4 except for using a bead mill for blending starting materials. Measurement by a laser-diffraction particle size distribution meter ("LA-920" available from HORIBA) revealed that this powder sample had a particle size of 0.8 μm.

EXAMPLE 21

Figure 4:
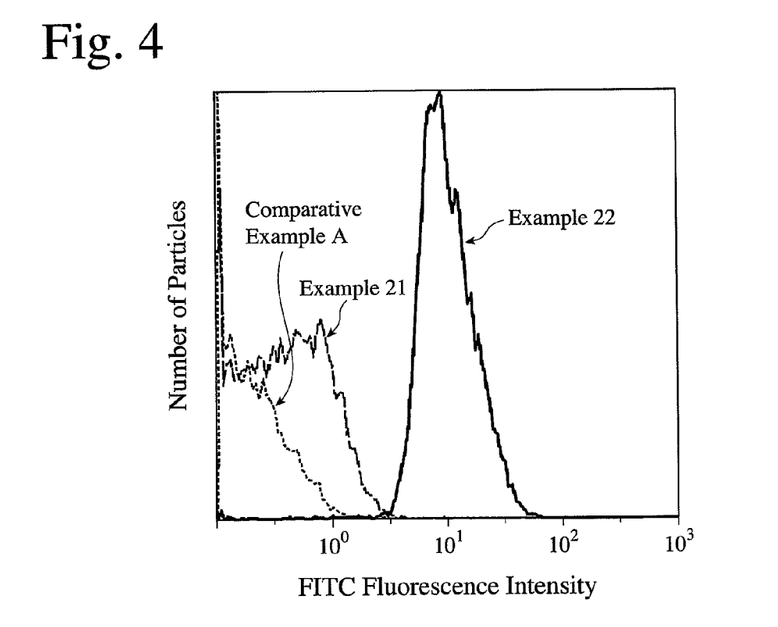
FIG. 4 is a graph showing the relation between FITC fluorescence intensity and the number of particles in the flow cytometry measurement of Examples 21 and 22 and Comparative Example A.

Silica coating was conducted in the same manner as in Example 15 except for using the coated, fine metal particles obtained in Example 20, to obtain silica-coated, fine metal particles. 0.1 g of the silica-coated, fine metal particles were mixed with 2 mL of an aqueous solution of 3-aminopropyl-triethoxysilane (APS), and stirred for 1 hour. They were dried in the air to obtain amino-group-fixed magnetic beads (amino-group-coated magnetic beads). Using BioMag Plus Amine Particle Protein Coupling Kit available from Bang Laboratories, streptavidin was fixed to the amino-group-coated magnetic beads by the following procedure. First, 15 mg of amino-group-coated magnetic beads and 600 μL of glutaric aldehyde adjusted to 5% by a pyridine wash buffer (PWB) attached to the kit were mixed, and stirred at room temperature for 3 hours. Non-magnetic components were removed from the resultant dispersion by magnetic separation, and the magnetic beads were washed with PWB 4 times. The resultant dispersion of magnetic beads in PWB was mixed with streptavidin (available from Wako Pure Chemical Industries, Ltd.), and stirred at 4° C. for 16 hours. 600 μL of a quenching solution attached to the kit was added to the dispersion, and stirred at room temperature for 30 minutes. By magnetic separation to remove non-magnetic components and washing with PWB 4 times, streptavidin-fixed, coated, fine metal particles (streptavidin-coated magnetic beads) were obtained. After the coated, fine metal particles were stained with biotinylated fluorescein isothiocyanate (FITC) (fluorescein biotin available from Molecular Probes), the amount of streptavidin fixed was measured by flow cytometry using a flow cytometer EPICS ALTRA® available from Beckman Coulter, Inc. The results are shown in FIG. 4.

EXAMPLE 22

An amino group was introduced by the same method as in Example 21, a carboxyl group was fixed using succinic anhydride, and streptavidin was fixed by activation with carbodiimide. After stained with biotinylated FITC in the same manner as in Example 21, the amount of streptavidin fixed was measured by flow cytometry. The results are shown in FIG. 4.

The flow cytometer is an apparatus for measuring fluorescence intensity of each particle. The fact that a histogram obtained by the measurement of large numbers of particles is shifted toward higher fluorescence intensity indicates that more fluorescent materials existed on the particle surfaces. It is also known that biotin tends to bond to streptavidin, forming a biotin-avidin bond. The streptavidin-fixed magnetic beads were reacted with the biotinylated FITC and then measured by a flow cytometer. The resultant histogram was shifted toward higher intensity of FITC fluorescence. This indicates that more streptavidin was fixed to the particle surfaces.

As is clear from FIG. 4, the streptavidin-coated magnetic beads of Examples 21 and 22 had higher intensity of FITC fluorescence than that of the coated, fine metal particles of Comparative Example A onto which streptavidin was not fixed (coated, fine metal particles obtained by coating the coated, fine metal particles of Example 20 with silica), indicating that streptavidin was fixed to the former.

EXAMPLE 23

Figure 5:
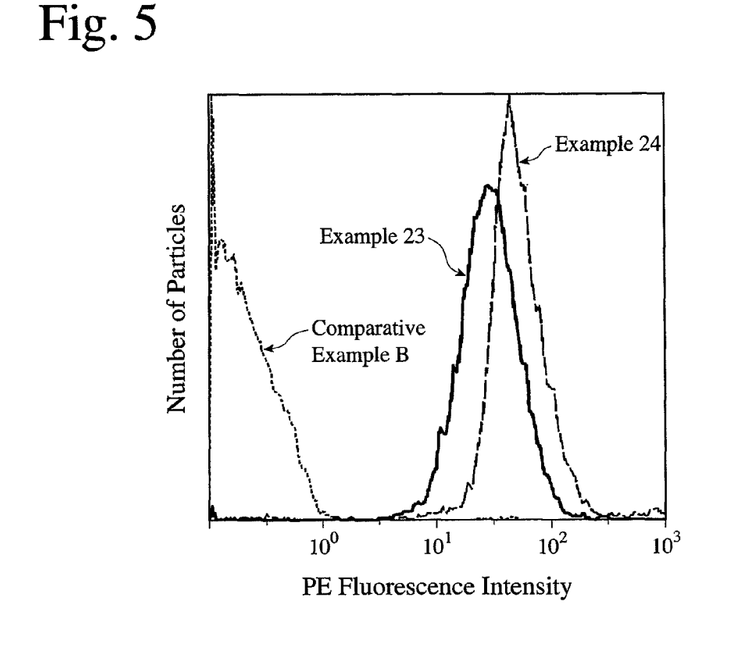
FIG. 5 is a graph showing the relation between FITC fluorescence intensity and the number of particles in the flow cytometry measurement of Examples 23 and 24 and Comparative Example B.

The streptavidin-coated magnetic beads of Example 21 were reacted with biotinylated antibody (Epithelial Specific Antigen-Biotin Labeled, Affinity Pure available from Biomeda) to obtain antibody-fixed, coated, fine metal particles (antibody-fixed magnetic beads). The antibody-fixed magnetic beads were stained with secondary antibody [PE-labeled, Goat F(ab')$_2$ Anti Mouse IgG (H+L) available from Beckman Coulter], and measured by flow cytometry. The results are shown in FIG. 5.

EXAMPLE 24

Antibody (VU-1D9)-fixed, coated, fine metal particles (antibody-fixed magnetic beads) were obtained in the same manner as in Example 22 except for using the antibody of VU-1D9 in place of streptavidin. The antibody-fixed magnetic beads were stained with secondary antibody [PE-labeled, Goat F(ab')$_2$ Anti Mouse IgG (H+L) available from Beckman Coulter], and measured by flow cytometry. The results are shown in FIG. 5.

The secondary antibody is selectively bonded to the antibody. The antibody-fixed magnetic beads were reacted with PE secondary antibody and measured by flow cytometer. The fact that the resultant histogram was shifted toward higher intensity of PE fluorescence indicates that more antibody was fixed to the particle surfaces.

As is clear from FIG. 5, the antibody-fixed magnetic beads of Examples 23 and 24 had higher intensity of PE fluorescence than that of the coated, fine metal particles of Comparative Example B (coated, fine metal particles obtained in Example 21), onto which the antibody was not fixed, indicating that the antibody was fixed to the former.

EXAMPLE 25

Coated, fine metal particles, onto which mouse IgG antibody was fixed, were produced in the same manner as in Example 22 except for using Mouse IgG antibody in place of streptavidin, and immersed in a solution of a blocking agent ("Block Ace" available from Snow Brand Milk Products Co., Ltd.) overnight to obtain blocking-agent-coated magnetic beads. Example 25A stained with secondary antibody [PE-labeled, Goat F(ab')2 Anti Mouse IgG (H+L) available from Beckman Coulter] specifically reacting with the fixed mouse IgG antibody, Example 25B stained with secondary antibody [PE-labeled, Goat F(ab')$_2$ Anti Mouse IgM available from Beckman Coulter] not specifically reacting with the fixed antibody, and Comparative Example C not stained with secondary antibody were measured by flow cytometry. The results are shown in FIG. 6.

Figure 6:
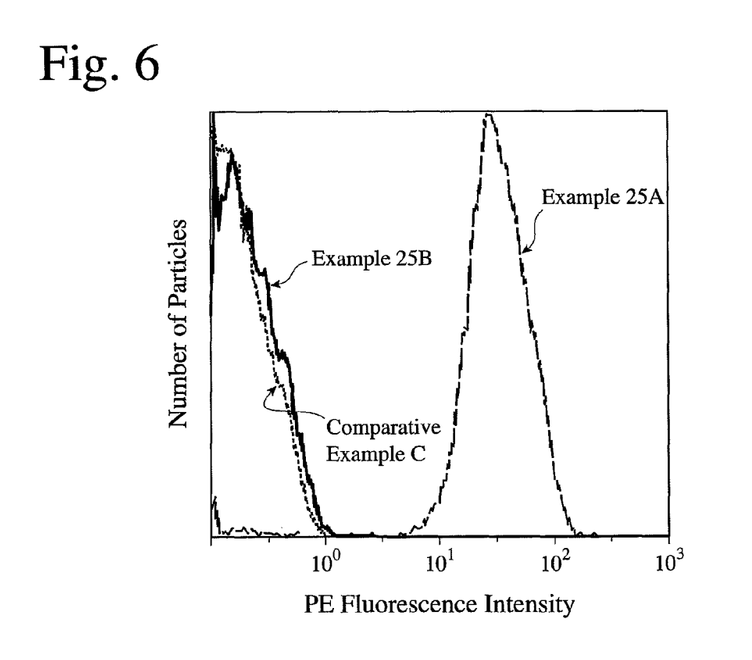
FIG. 6 is a graph showing the relation between PE fluorescence intensity and the number of particles in the flow cytometry measurement of Examples 25A and 25B and Comparative Example C.

As is clear from FIG. 6, the blocking-agent-coated magnetic beads of Example 25 reacted only with the specifically reactable secondary antibody. It was thus found that nonspecific adsorption did not occur.

EXAMPLE 26

Figure 7:
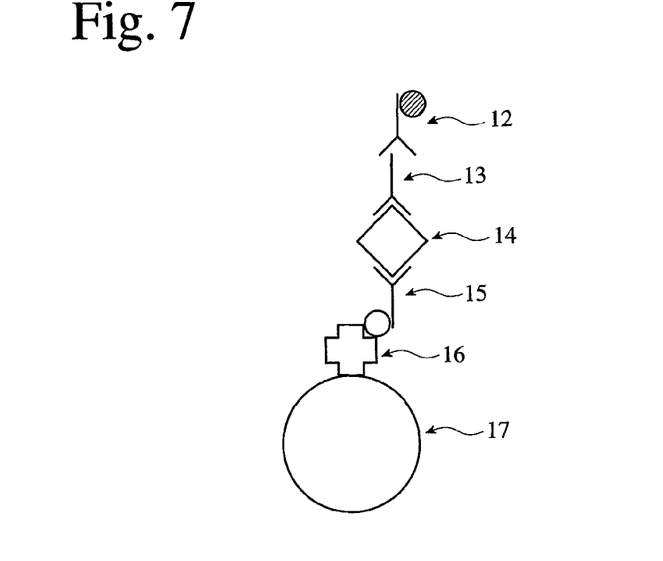
FIG. 7 is a schematic view showing ELISA produced by the coated, fine metal particle.

As shown in FIG. 7, the coated, fine metal particles 17 of Example 22, onto which streptavidin 16 was fixed, were incubated with biotin-labeled, anti-human adiponectin antibody (mouse) 15 ("Biotin-Labeled, Anti-Human Adiponectin/Acrp30 Antibody" available from R&D SYSTEMS) for 30 minutes to obtain the coated, fine metal particles 17, onto which the antibody 15 was fixed. Using the coated, fine metal particles 17, sandwich ELISA (enzyme-linked immunosorbent assay) was conducted. First, the coated, fine 20 metal particles 17 onto which the antibody 15 was fixed and the human adiponectin 14 ("Human Adiponectin, His-Tagged Fusion Protein" available from BioVendor) were incubated. After the coated, fine metal particles 17 were incubated with anti-human adiponectin antibody (rabbit) (first antibody liquid) 13 attached to the Human Adiponectin ELISA Kit (Otsuka Pharmaceutical Co., Ltd.) and washed, they were incubated with horseradish peroxidase (HRP)-labeled, rabbit IgG polyclonal antibody (goat) (enzyme-labeled antibody solution) 12 and washed. After reaction with a substrate, the reaction was terminated with a reaction termination liquid to measure signal intensity (absorbance at 450 nm) by a UV spectrometer. The same operation was conducted with the concentration of the human adiponectin 14 changed, to obtain the relation between the concentration of the human adiponectin 14 and signal intensity. The results are shown in FIG. 8.

Figure 8:
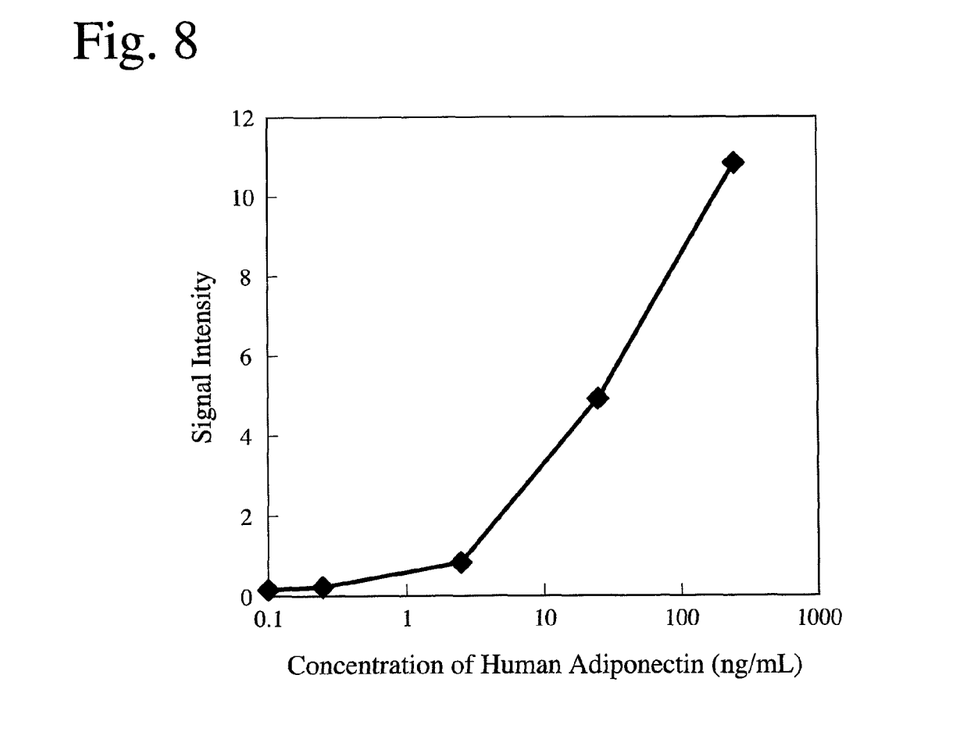
FIG. 8 is a graph showing the relation between the concentration of human adiponectin and signal intensity in Example 26.

As is clear from FIG. 8, there was a correlation between the concentration of human adiponectin and the signal intensity. After calibration is prepared using a human adiponectin solution having a known concentration, a human adiponectin solution having an unknown concentration can be measured to determine the concentration of human adiponectin from the measured signal intensity. It has thus been found that the coated, fine metal particles of the present invention are suitable for immunoassay.

EXAMPLE 27

Coated, fine metal particles, onto which biotin-labeled, anti-human adiponectin antibody (mouse) was fixed, were produced in the same manner as in Example 26, except for using the magnetic silica particles of Example 19. Using the above coated, fine metal particles, sandwich ELISA (enzyme-linked immunosorbent assay) was conducted in the same manner as in Example 26. The results are shown in FIG. 9.

EXAMPLE 28

Coated, fine metal particles, onto which biotin-labeled, anti-human adiponectin antibody (mouse) was fixed, were produced in the same manner as in Example 26 except for using the magnetic silica particles of Example 18. Using the above coated, fine metal particles, sandwich ELISA (enzyme-linked immunosorbent assay) was conducted in the same manner as in Example 26. The results are shown in FIG. 9.

Figure 9:
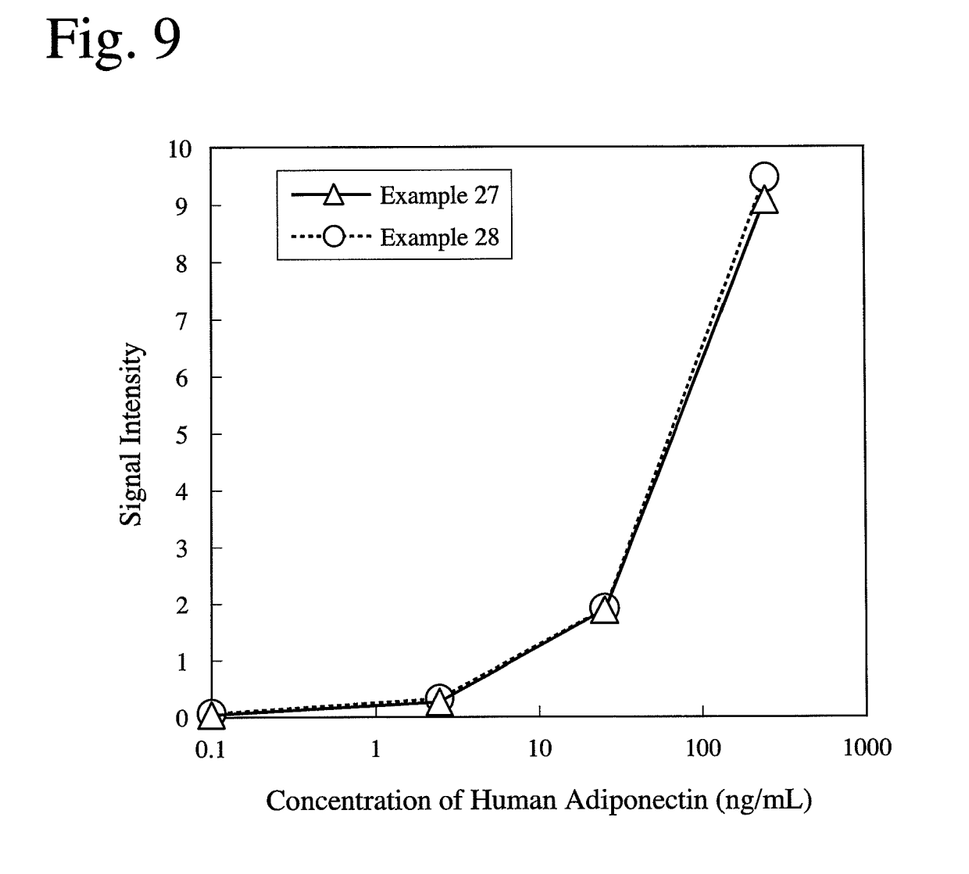
FIG. 9 is a graph showing the relation between the concentration of human adiponectin and signal intensity in Examples 27 and 28.

As is clear from FIG. 9, there was a correlation between the concentration of human adiponectin and the signal intensity. It has thus been found that the coated, fine metal particles of the present invention are suitable for immunoassay.

EFFECT OF THE INVENTION

The method of the present invention can produce coated, fine metal particles having excellent corrosion resistance easily at low cost. The coated, fine metal particles of the present invention contain less C and N elements, and act as magnetic particles having high saturation magnetization when Fe and/or Co are used for metal core particles. Because the magnetic metal particles are coated with a Ti oxide layer having high corrosion resistance, they are suitable for nucleic-acid-extracting magnetic beads, which need high corrosion resistance because they are used in a corrosive solution, etc.

What is claimed is:

1. Coated, fine metal particles each comprising a metal core particle and a Ti oxide coating, said metal particles having a carbon content of 0.2-1.4% by mass and a nitrogen content of 0.01-0.2% by mass.

2. The coated, fine metal particles according to claim 1, wherein the carbon content is 0.2-1.1% by mass, and the nitrogen content is 0.04-0.12% by mass.

3. The coated, fine metal particles according to claim 1, wherein the total content of carbon and nitrogen is 0.24-0.60% by mass.

4. The coated, fine metal particles according to claim 1, wherein said metal comprises at least one element selected from the group consisting of Fe, Co and Ni.

5. The coated, fine metal particles according to claim 1, wherein said metal comprises Fe.

6. The coated, fine metal particles according to claim 5, wherein the Fe content is 14-20 atomic % in the quantitative analysis of O, Ti and Fe by X-ray photoelectron spectroscopy, the ratio of metal Fe being 7-11% of the entire Fe.

7. The coated, fine metal particles according to claim 5, wherein when 25 mg of said coated, fine metal particles are immersed in 1 mL of an aqueous solution of guanidine hydrochloride having a concentration of 6 M at 25° C. for 24 hours, the amount of Fe ions eluted is 50 mg/L or less.

8. The coated, fine metal particles according to claim 1, which are treated with an alkali.

9. The coated, fine metal particles according to claim 1, onto which at least one selected from the group consisting of an amino group, a carboxyl group, an aldehyde group, a thiol group, a tosic group and a hydroxyl group is fixed.

10. The coated, fine metal particles according to claim 1, onto which a ligand is fixed.

11. The coated, fine metal particles according to claim 1, which are further coated with a blocking agent.

12. The coated, fine metal particles according to claim 1, which are coated with silicon oxide.

13. The coated, fine metal particles according to claim 12, onto which at least one selected from the group consisting of an amino group, a carboxyl group, an aldehyde group, a thiol group, a tosic group and a hydroxyl group is fixed.

14. The coated, fine metal particles according to claim 13, onto which a ligand is fixed.

15. The coated, fine metal particles according to claim 14, which are further coated with a blocking agent.

\* \* \* \* \*